United States Patent [19]

Mancini et al.

[11] 4,056,496

[45] * Nov. 1, 1977

[54] HYDROGELS AND ARTICLES MADE THEREFROM

[75] Inventors: William L. Mancini, Framingham; Donald R. Korb, Boston; Miguel F. Refojo, Lexington, all of Mass.

[73] Assignee: Corneal Sciences, Inc., Burlington, Mass.

[*] Notice: The portion of the term of this patent subsequent to May 18, 1993, has been disclaimed.

[21] Appl. No.: 685,996

[22] Filed: May 13, 1976

Related U.S. Application Data

[63] Continuation-in-part of Ser. No. 451,906, March 18, 1974, Pat. No. 3,957,362, which is a continuation-in-part of Ser. No. 294,019, Oct. 2, 1972, abandoned.

[51] Int. Cl.$^2$ .................. C08F 220/14; G02C 7/04
[52] U.S. Cl. ..................... 260/29.6 TA; 128/130; 264/1; 260/2.5 R; 351/160; 424/81; 526/230; 526/273; 526/320
[58] Field of Search ............. 351/160; 264/1; 424/81; 128/130; 526/230, 320, 273; 260/29.6 TA

[56] References Cited

U.S. PATENT DOCUMENTS

| | | | |
|---|---|---|---|
| 2,976,576 | 3/1961 | Wichterle et al. | 264/1 |
| 3,220,960 | 11/1965 | Wichterle | 260/2.5 |
| 3,957,362 | 5/1976 | Mancini et al. | 351/160 |

OTHER PUBLICATIONS

Yasuda et al., Die Makromolekulare Chemie 118 (1968) pp. 19 & 22-24.
Yasuda et al., J. Pol. Sci., Part A-2, vol. 9 (1971) pp. 1117 & 1122-1124.

*Primary Examiner*—Harry Wong, Jr.
*Attorney, Agent, or Firm*—Dike, Bronstein, Roberts, Cushman & Pfund

[57] ABSTRACT

This invention relates to polymers and hydrogels of polymers formed from a hydrophilic monomer of the group of dihydroxyalkyl acrylates and methacrylates, a substantially water insoluble monomer from the group of alkyl acrylates and methacrylates and preferably a minor amount of a water insoluble epoxidized alkyl acrylate or methacrylate. The hydrogels are preferably used for the formation of contact lenses, but may also be used for drug and pesticides delivery devices: dialysis, ultrafiltration and reverse osmosis membranes; implants in surgery and dentistry, and the like.

29 Claims, No Drawings

HYDROGELS AND ARTICLES MADE THEREFROM

CROSS REFERENCE TO RELATED APPLICATIONS

This application is a continuation-in-part of copending U.S. application Ser. No. 451,906 filed Mar. 18, 1974, now U.S. Pat. No. 3,957,362 which is in turn a continuation-in-part of U.S. Pat. application Ser. No. 294,019 filed Oct. 2, 1972, now abandoned.

BACKGROUND OF THE INVENTION

1. Introduction

This invention relates to polymers and hydrogels of polymers from alkyl acrylates or methacrylates, dihydroxyalkyl acrylates or methacrylates and epoxidized acrylates or methacrylates. The hydrogels are particularly useful for the formation of contact lenses.

2. Description of the Prior Art

As is known in the art, contact lenses are frequently made from polymethyl methacrylate. Such lenses are known as the "hard lenses". Many people cannot adapt to the presence of the hard lens in the eye and with other, the lens compromises the physiological processes required for corneal metabolism. For many, minor irritations are caused by small particles that become lodged under the hard lens resulting in irritation of the cornea. Moreover, it has been found that after wearing a hard lens for an extended time — e.g., from one to five years, many people experience discomfort and are forced to discontinue its use.

In view of the above difficulties, an effort has been made to develop new lens materials which overcome the problems of the hard lens. One class of such lens materials is described in U. S. Pat. Nos. 2,976,576 and 3,220,960 incorporated herein by reference. These materials are hydrogels of a sparingly cross-linked hydrophilic copolymer, of a major amount of a monoester of an olefinic acid selected from the group of acrylic and methacrylic acids having a single olefinic double bond and a minor amount of a polymerizable diester of one of said acids, the diester having at least two olefinic double bonds. The copolymer is formed by copolymerization in a solvent medium.

One specific hydrogel disclosed in the aforesaid patents is a slightly cross-linked material comprising a predominant quantity of 2-hydroxyethyl methacrylate. This hydrogel, known as "Hema" is used for contact lens fabrication in part, because of its ability to absorb water of hydration, typically from about 35 to 65 percent by weight. The water renders the lens flexible and soft, which enables it to mold to the curvature of the eye. This is in contrast to the conventional hard lens which maintains a rigid configuration that does not always conform to the eye's curvature.

An advantage of the Hema lens is that with proper design, it can be worn with almost immediate comfort. Another advantage is that relative to the hard lens, the difficulties resulting from particles lodging beneath the lens irritating the cornea is reduced.

Despite the above advantages, there are problems that have prevented universal acceptance of the Hema lens. One problem involves a lack of clarity of central vision. For many, the Hema lens does not give steady vision because a constantly changing optical surface results from eye movement and blinking. A second problem pertains to astigmatism. Hard lenses correct astigmatism by providing a new surface on the cornea. Because of the flexibility of the Hema lens, it conforms to the shape of the eye and frequently does not provide the new surface necessary to correct astigmatism. Other difficulties are experienced with use of the Hema lens such as corneal irritation and folds in the membrane of the eye. The exact causes are not known though it has been reported that lacrimal interchange with the Hema lens is minimal compared to the hard lens, possibly due to lens conformation to the contour of the eye which prevents flow of lacrimal fluid beneath the edges of the lens. A reduction in lacrimal fluid reduces the flow of oxygen to the cornea and relief from an accumulation of catabolic products. Finally, the Hema lens has been reported to tear easily.

As will be discussed in greater detail below, the subject hereof is new hydrogel having utility including use as a soft contact lens. The hydrogel is formed from a dihydroxyalkyl acrylate or methacrylate, an alkyl acrylate or a methacrylate, and preferably, a minor amount of an epoxidized alkyl acrylate or methacrylate. The hydrogel is formed by bulk polymerization and is characterized by insolubility in water and many solvents. The preferred monomers are glyceryl methacrylate, methyl methacrylate and glycidyl methacrylate within a given range of ratios. Copolymers that are solvent soluble, but water insoluble formed from glyceryl methacrylate and methyl methacrylate are known and described by H. Yasuda, C. E. Lamaza, and L. D. Ikenberry, Makromol. Chem. 118, 1935 (1968) and H. Yasuda, C. E. Lamaza, and A. Peterlin, J. Polym. Sc. Part A-2, 996, 1,117–1,131 (1971).

The copolymers described in the first of these publications are polymerized in a 70/30 acetic acid/water solvent system. The solutions are prepared with 5% by weight total monomer dissolved in 95% by weight solvent. After eight to ten days at room temperature, precipitation of the polymer is effected in water. Six copolymers are described having monomer mole ratios of methyl methacrylate and glyceryl methacrylate of from 95:5 to 70:30.

The procedure of the second publication is similar to that of the first except that the reaction is carried out in a nonaqueous solvent. For reasons below, the copolymers of these publications differ markedly from the hydrogels described herein and do not have properties suitable for formation of a contact lens.

SUMMARY OF THE INVENTION

The invention herein is a polymer and hydrogels thereof of a hydrophilic monomer from the group of dihydroxyalkyl acrylates and methacrylates (hereinafter collectively the "dihydroxyalkyl acrylate"), a substantially water insoluble monomer from the group of alkyl acrylates and methacrylates (hereinafter collectively "the acrylate") and preferably, a minor amount of an epoxidized alkyl acrylate or methacrylate (hereinafter collectively the "epoxidized acrylate").

The polymer is formed by a free radical, bulk polymerization process in the substantial absence of solvent as this procedure is required to form polymers having properties suitable for the formation of the devices disclosed herein, particularly for use as a contact lens material when hydrated. The dihydroxyalkyl acrylate is preferably used in major amount, the alkyl acrylate in minor amount and the epoxidized acrylate in an amount sufficient to impart desired rigidity.

The hydrogels from the polymers disclosed herein have some properties similar to Hema (described above) and are suitable for formation of contact lenses as well as other items assimilated with living tissue such as surgical implants. However, a lens formed from the hydrogels herein do not suffer many of the disadvantages of lenses formed from Hema. In this respect, though the hydrogels herein are soft and supple, they are stronger and stiffer than Hema. Consequently, they provide steady vision avoiding difficulties associated with a changing optical surface. Further, since the hydrogels herein are stiffer than Hema, a lens formed therefrom is capable of design with peripheral curvatures that maximize fluid flow and provides fresh lacrimal fluid to areas of the eye covered by the lens. The fluid provides oxygen and moves catabolic products from beneath the lens. Moreover, added stiffness permits fabrication of lenses of thinner cross-section than lenses formed from Hema. This results in substantial oxygen and carbon dioxide permeability needed for normal corneal physiology. In addition, thin lens fabrication permits the flow of lacrimal fluid beneath the edges of the lens which flow is believed to be a pumping action activated by blinking. Consequently, eye irritation is avoided and the lens can be worn for extended periods of time without removal -- e.g., up to six months' continuous wear. Other advantages of lenses formed from the hydrogels herein include improved ability to clean and a toughness that prevents tearing.

DESCRIPTION OF THE PREFERRED EMBODIMENTS

The hydrophilic dihydroxyalkyl acrylate comonomer conforms to the general formula:

$$CH_2=\overset{R}{\underset{|}{C}}-\overset{O}{\underset{\|}{C}}-O-(CH_2)_n-\overset{OH}{\underset{|}{CH}}-CH_2OH$$

where R is hydrogen or methyl and n is a whole integer having a value of from 0 to 4, preferably from 1 to 4.

The dihydroxyalkyl acrylate can be formed by hydrolysis following the procedures set forth in British Pat. No. 852,384 (incorporated herein by reference) where a dioxolanoalkyl acrylate or methacrylate is hydrolyzed with a dilute aqueous solution of a strong mineral acid for an extended period of time at about room temperature. This procedure is illustrated below.

EXAMPLE 1

Fifty grams of isopropylideneglyceryl methacrylate, 150 ml of water, 0.3 g. of concentrated sulfuric acid, and 0.02 of hydroquinone are stirred for 16 hours at 25°-30° C. A clear colorless solution forms. Sulfuric acid is neutralized by addition of barium hydroxide. The precipitate (barium sulfate) is removed by filtration and washed with water. The filtrate and washings are combined to give 212 ml of a clear, colorless solution, calculated to consist of a 20% solution of 2,3-dihydroxypropyl methacrylate in dilute aqueous acetone (12/1). The product is isolated by saturation with sodium chloride and extracted with benzene or ether. After stripping solvent at reduced pressure, 2,3-dihydroxypropyl methacrylate (glyceryl methacrylate) is obtained as a slightly viscous oil.

A preferred comonomer herein is glyceryl methacrylate. The monomer may be made by the above process, but is preferably prepared in accordance with the process described by M. F. Refojo, Journal of Applied Polymer Science, Volume 9, pp 3161 to 3170(1965) where glycidyl methacrylate is hydrolized and then solvent extracted as illustrated below.

EXAMPLE 2

One hundred grams of glycidyl methacrylate, 150 ml distilled water and 0.25 ml concentrated sulfuric acid are stirred for 6 days at room temperature.

Glycidyl methacrylate is immiscible with water, but its product, glyceryl methacrylate, is formed which is soluble and a clear solution is formed. The glyceryl methacrylate co-dissolves unreacted glycidyl methacrylate.

The reaction mixture is neutralized with a 10% sodium hydroxide solution and extracted with five 100 ml aliquots of ether. The extract is washed with three 20 ml portions of distilled water and the aqueous solution is washed with 50 ml of ether. The combined ether extracts are dried with anhydrous sodium sulfate. The ether is evaporated in a rotating evaporator. The residue (18.8 grams) from the ether extract is mainly glycidyl methacrylate suitable for preparation of additional glyceryl methacrylate.

The aqueous extract is saturated with sodium chloride with glyceryl methacrylate separating as an oily layer. This layer is dissolved in methylene chloride, dried with anhydrous sodium sulfate and evaporated using the above procedure. The residue (71.6g) is a viscous, clear liquid of glyceryl methacrylate containing some unreacted glycidyl methacrylate.

The concentration of glycidyl methacrylate remaining in the above reaction mixture following solvent extraction is dependent upon the extraction efficiency, the concentration typically varying between about 1.8 to 2.2 percent of the total glyceryl methacrylate for the procedure described, but being capable of reduction to essentially 0 with a more efficient solvent such as methylene chloride in place of the ether.

Other dihydroxyalkyl acrylates can be made from their corresponding epoxy alkyl esters by the process described in the above examples, the examples being set forth for purposes of illustration only.

The second comonomer is a substantially water insoluble alkyl acrylate or methacrylate corresponding to the general formula:

$$CH_2=\overset{R}{\underset{|}{C}}-\overset{O}{\underset{\|}{C}}-OR'$$

where R is hydrogen or methyl and R' is alkyl having from 1 to 6 carbon atoms. Alkyl acrylates conforming to this formula are readily available. Examples of suitable acrylates include methyl acrylate, methyl methacrylate, ethyl acrylate, ethyl methacrylate, propyl methacrylate, butyl acrylate and butyl methacrylate. Methyl methacrylate is most preferred.

The third comonomer is the epoxidized alkyl acrylate conforming to the formula $$CH_2=\overset{R}{\underset{|}{C}}-\overset{O}{\underset{\|}{C}}-O-(CH_2)_n-\overset{O}{\overset{/\ \backslash}{CH-CH_2}}$$

where R and n are as above defined. Examples of suitable epoxidized acrylates include 2,3-epoxypropyl acrylate, 2,3-epoxypropyl methacrylate, and the like.

The preferred epoxidized acrylate is that used to form the dihydroxy acrylate if the procedures of Example 2 are employed. Thus, the epoxidized acrylate is preferably the source of the hydroxy acrylate monomer.

The molar ratio of dihydroxyalkyl acrylate to alkyl acrylate can vary within broad limits dependent upon the use to which the material is to be put. Preferably the ratio varies within the range of from 1:3 and 20:1. Preferably, the dihydroxyalkyl acrylate at least equal or exceeds the alkyl acrylate and a preferred ratio varies between about 1:1 10:1, more preferably between 1.2:1.0 and 2:1. For use of the hydrogel as a contact lens material, the most preferred molar ratio is about 1.5:1.0.

The amount of epoxidized acrylate used may vary within broad parameters, generally from 0 to 30% by weight of the dihydroxy acrylate, more preferably, from 0.1 to 15% by weight and most preferably, from 3.2 to 7.5% dependent upon the monomers used, their ratio and the like. A more definite amount is the amount sufficient to provide a polymer capable of adsorbing water of hydration in an amount of from 35 to 50%, and more preferably, from 42 to 46%.

It is believed that the epoxidized acrylate acts as a crosslinking agent for the polymer. In this respect, other crosslinking agents may be included in the formulation such as diesters of acrylic and methacrylic acid as well as derivatives thereof such as triethanolamine dimethacrylate, triethanolamine trimethacrylate, tartaric acid dimethacrylate, triethylene glycol dimethacrylate, the dimethacrylate of bis-hydroxyethylacetamide, and the like. The amount of crosslinking agent is dependent upon the desired properties of the polymer. In general, the concentration should not exceed 5% of the total monomer constituents and should be sufficient to yield a hydrogel from the polymer having the above hydration properties.

The hydrogels are formed by bulk polymerization using suitable catalysts. The monomers are mixed in the absence of solvent and maintained under reduced pressure at an elevated temperature for a period of time sufficient to solidify the reaction mixture. Typically, the temperature of reaction varies between 20° and 60° C, preferably between 35° and 42° C and most preferably is maintained at about 40° C. The catalyst concentration may vary within broad limits dependent upon the particular catalyst used, but generally varies between about 0.001 and 0.2 weight percent of the hydroxyalkyacrylate, and preferably between 0.01 and 0.04 weight percent. A preferred catalyst is isopropyl percarbonate in an amount of about 0.02 weight percent.

The epoxidized acrylate comonomer may be present in the dihydroxy acrylate if formed by hydrolysis of its epoxy precursor as in Example 2, if not removed completely by solvent extraction. This is in part due to the dihydroxyalkyl acrylate being a cosolvent for the epoxy acrylate in the aqueous phase. If the amount of epoxidized acrylate remaining after extraction is less than the amount required, its concentration can be increased by addition of additional epoxidized acrylate or by other conventional crosslinking agents such as those described above.

For use as a contact lens, the hydrogels preferably have certain properties. The present hydration with water has been discussed above. Preferably, the percent hydration varies between 35 and 50% by weight and more preferably, from 42 to 46%. Another important property is the percent linear elongation. Preferably, the hydrated gel will exhibit a linear expansion of from 15 to 25% and more preferably, from 18 to 21%. A final important property is its hardness. Preferably, it has a Shore A durometer Type A-2 reading (ASTM Designation D2240-68) of from 40 to 50 and more preferably, from 42 to 47.

As to the degree of crosslinking of the gels from the polymers described herein, a guide to the extent of crosslinking is the solubility properties of the gels in various organic solvents. In general, the gels are insoluble in solvents such as dioxane, acetone, methylene chloride and mixtures thereof. In fact, no solvent has as yet been found that dissolves the gels though it is obvious that not all solvents have been tested.

The specific properties of a hydrogel in accordance with this invention are of course dependent upon the specific monomers used, the ratios thereof and the concentrations of crosslinking agent. In general, a hydrogel exhibiting the aforesaid properties may be obtained by following the most preferred embodiments of the invention described herein.

EXAMPLE 3

A mixture of 56.8 g. 2,3-dihydroxypropyl methacrylate (GMA-made in accordance with Example 2 above and containing 1.28% glycidyl methacrylate) and 23.7 g. of methyl methacrylate (MMA-mole ratio of 1.5:1.0) is stirred and 3 g. of sodium sulfate added to remove traces of water. The mixture is filtered and 15.5 mg of isopropyl percarbonate added. The mixture is stirred thoroughly and transferred to a large tube.

The tube is then put in a low temperature bath, purged with nitrogen three times, sealed under vacuum and placed in a constant temperature bath at between 35° and 40° C whereby polymerization occurs. Temperature is maintained for about five hours, though after about the first 90 to 95 minutes, the mixture had solidified indicating that reaction had taken place. The time for solidification will hereinafter be referred to as the "polymerization time". After five hours, the tube is placed in an oven maintained at 75° C for 16 hours (overnight). The temperature is then raised to 90° C and held at this temperature for one hour.

The polymer formed above can be removed from the tube in the form of a solid rod. When cut into thin discs or shaped into the form of a lens and placed in water, it becomes hydrated and develops a soft, rubbery consistency.

EXAMPLES 4 - 8

The procedure of Example 3 is repeated with variations in the ratio of GMA to MMA. The catalyst concentration is held constant at 0.02 weight percent based upon the weight of the GMA. The polymerization temperature is held at 40° C. Following the reaction, the polymer is evaluated by percent hydration, percent linear swelling, durometer hardness and appearance, all properties being measured in the hydrated state. The results are set forth in the following table:

| Ex. No. | Ratio GMA: MMA | Hydration (percent) | Linear Swelling[1] | Durometer[2] | Appearance[3] |
|---|---|---|---|---|---|
| 4 | 1:1 | 27–29 | 12–14 | — | VM |
| 5 | 1.25:1 | 33–35 | 14–16 | 53–56 | VM |
| 6 | 1.5:1 | 39–42 | 17–19 | 46–49 | SM |
| 7 | 2:1 | 43–45 | 20–22 | 39–43 | SC |

-continued

| Ex. No. | Ratio GMA: MMA | Hydration (percent) | Linear Swelling[1] | Durometer[2] | Appearance[3] |
|---|---|---|---|---|---|
| 8 | 3:1 | 50–52 | 25–27 | — | C |

[1]As used throughout the balance of this specification, linear swelling (percent).
[2]As used throughout the balance of this specification, durometer reading —Shore Durometer Type A-2(0–60) ASTM D 2240-68.
[3]As used throughout the balance of this specification, appearance determined by viewing a round button, 3mm thick having a 12mm diameter through the edge or cross-section of the button. the symbols used and their meaning are as follows: VM—very milky, SM—slightly milky, SC—slightly clear, C—clear Example 6 is preferred for use as a contact lens even though slightly milky when viewed through the cross-section of the button. This preference is based upon the combination of hardness and rigidity properties which are optimum for the fabrication of a lens. As to optical clarity of a lens fabricated from the preferred polymers, in the thin cross-sections of the lens (0.05 to 0.15 mm), the slightly milky appearance is not evident.

EXAMPLES 9 – 14

The procedure of example 3 is repeated with the concentration of catalyst increased. The increase results in an expected decreased reaction time as shown in the following table:

| Ex. No. | Catalyst Percent | Time (Min.) | Hydration (percent) | Linear Swelling | Durometer | Appearance |
|---|---|---|---|---|---|---|
| 9 | 0.02 | 93 | 39–42 | 17–19 | 46–49 | SM |
| 10 | 0.03 | 60 | 41 | 20 | 46 | SM |
| 11 | 0.04 | 45 | 41 | 18 | 47 | SC |
| 12 | 0.05 | 34 | 40 | 20 | 47 | SC |
| 13 | 0.06 | 28 | 41 | 20 | 47 | C |
| 14 | 0.08 | 18 | 42 | 20 | 46 | C |

EXAMPLES 15 – 17

The procedure of Example 3 is repeated with temperature varied, all other conditions being held constant, with results as follows:

| Ex. No. | Temp. °C. | Time (Min.) | Hydration (percent) | Linear Swelling | Durometer | Appearance |
|---|---|---|---|---|---|---|
| 15 | 40 | 93 | 39–42 | 17–19 | 46–49 | SM |
| 16 | 43 | 42 | 41 | 20 | 47 | SC |
| 17 | 45 | 39 | 42 | 20 | 46 | SC |

EXAMPLE 18

The procedure of Example 13 may be repeated substituting ethyl methacrylate for methyl methacrylate with similar results.

EXAMPLE 19

The procedure of Example 3 may be repeated substituting methyl acrylate for methyl methacrylate with similar results.

EXAMPLE 20

The procedure of Example 3 may be repeated substituting 2,3-dihydroxypropyl acrylate for 2,3-dihydroxypropyl methacrylate with similar results.

EXAMPLE 21

The procedure of Example 3 may be repeated substituting glyceryl acrylate containing glycidyl acrylate for the glyceryl methacrylate.

EXAMPLE 22

Two hundred grams (1.406 mole) of glycidyl methacrylate, 300 ml of water and 0.5 ml of concentrated sulfuric acid are stirred for 5 days at 24–29° C. A clear solution forms having a pH of 2.0 which is neutralized with 10% sodium hydroxide. The solution is extracted with six 100 ml portions of ethyl ether. The aqueous layer is stirred and saturated with sodium sulfate which is then extracted with six 100 ml portions of methylene chloride. The methylene chloride extracts are concentrated under reduced pressure to yield 118.7 grams of glyceryl methacrylate containing 2.19% unreacted glycidyl methacrylate. 62.6 gm of this material is mixed with 26.1 gm of methyl methacrylate. The mixture is combined with 18.2 mg of isopropyl percarbonate, and separated into four test tubes. Nitrogen is bubbled through each tube, the tubes arecooled to − 30° C, evacuated, filled with nitrogen, sealed under vacuum, and put into a constant temperature bath at 40° C for 5 hours. The tubes are then put in an oven held at 75° C overnight. The next morning, the temperature is increased to 90° C for one hour. The tubes are then cooled and broken to provide a solid rod of polymer.

EXAMPLE 23

The procedure of Example 2 is repeated substituting methylene chloride in the first extraction step (following hydrolysis) for ethyl ether. This change in procedure results in a substantial reduction in the glycidyl methacrylate content found in the glyceryl methacrylate.

EXAMPLE 24

The procedure of Example 3 is repeated using the GMA of Example 23 and adding glycidyl methacrylate to the reaction mixture in varying concentrations (based upon the concentration of GMA) with results as follows:

| Example No. | Percent glycidyl methacrylate | Percent Hydration |
|---|---|---|
| 23 | 1.16 | 49.2 |
| 24 | 3.04 | 43.9 |
| 25 | 3.58 | 43.7 |
| 26 | 4.27 | 42.6 |
| 27 | 4.48 | 40.2 |
| 28 | 5.44 | 40.1 |
| 29 | 7.00 | 39.3 |
| 30 | 8.70 | 39.0 |
| 31 | 16.70 | 35.5 |
| 32 | 22.90 | 30.0 |
| 33 | 53.70 | 24.2 |

EXAMPLE 34 – 40

The procedure of Example 3 is repeated but using ethylene glycol dimethacrylate (EGDMA) first, then tetraethyleneglycol dimethacrylate (TEGDMA) as added crosslinking agent. The results are as follows where concentrations are weight percentages based upon the GMA.

| Example No. | EGDMA | TEGDMA | Percent Hydration |
|---|---|---|---|
| 34 | 0.70 | — | 43.7 |
| 35 | 1.40 | — | 40.4 |
| 36 | 2.10 | — | 38.4 |
| 37 | — | 0.7 | 44.5 |
| 38 | — | 1.4 | 42.1 |
| 39 | — | 2.1 | 41.4 |

| Example No. | EGDMA | TEGDMA | Percent Hydration |
|---|---|---|---|
| 40 | — | — | 46.8 |

EXAMPLE 41 – 47

The procedure of Example 3 is repeated using GMA containing 1.33% glycidyl methacrylate (based upon the weight of GMA) to which 2,3-epoxypropyl acrylate is added in varying concentrations (based upon the weight of GMA) with results as follows:

| Example No. | Concentration(%) | Percent Hydration |
|---|---|---|
| 41 | 1.33 | 48.5 |
| 42 | 2.77 | 45.6 |
| 43 | 3.62 | 44.9 |
| 44 | 5.81 | 42.4 |
| 45 | 10.35 | 39.7 |
| 46 | 24.00 | 27.5 |
| 47 | 52.60 | 19.9 |

As discussed above, the hydrogels herein have properties rendering them useful for soft contact lens fabrication. After absorbing water (or physiological saline water or water containing a physiologically active solute such as a bacteriostatic agent), the hydrogels are soft and flexible, though tough and tear resistant. They are more rigid than Hema and consequently, provide contact lenses with improved optical performance. They may be fabricated in thinner cross-section, typically in cross-sections of from 0.05 to 0.15 mm. Consequently, they are more permeable to oxygen and carbon dioxide. The increased rigidity of the hydrogel reduces deformation (rippling) of the lens due to blinking, thus preventing a changing optical surface. This avoids variations and distortions in vision. Further, with proper design, lenses from the hydrogels are sufficiently rigid to maintain their shape thus permitting a flow of lacrimal fluid beneath the lens by a pumping action activated by blinking. This provides fresh lacrimal fluid and oxygen to those areas covered by the lens and relieves catabolic products that might otherwise accumulate.

The materials disclosed herein have physiochemical properties rendering them suitable for prolonged contact with living tissue, blood and the mucous membrane such as would be required for surgical implants, blood dialysis devices and the like. It is known that blood, for example, is rapidly damaged in contact with artificial surfaces. The design of a synthetic surface which is antithrombogenic and nonhemolytic to blood is necessary for prosthesis end devices used with blood. The hydrogels herein are non-ionic and rich in water as is living tissue. Hence, they have a tendency to reduce clotting of blood as occurs when blood contacts other hydrophobic artificial surfaces.

The hydrogels are selectively permeable to water and qualify for applications involving dialysis, ultrafiltration and reverse osmosis. The good chemical stability of the hydrogels also make them suitable for electrolytic purposes.

The hydrogels herein can be impregnated with a solution containing a drug. An article from the hydrogel such as an intrauterine device, can then be administered to a patient and the drug will gradually be released to the patient. As the drug is rinsed from the surface of the hydrogel, it will be replaced with a fresh supply of drug migrating to the surface thereof from its interior.

The hydrogels herein can be boiled and/or autoclaved in water without being damaged whereby thorough sterilization may be achieved. Thus, an article formed from the hydrogel may be used in surgery where an article compatible with living tissue or with the mucous membrane may be used, e.g., — for making contact lenses as described above, for filling or dividing cavities in tissue, for pessaries, and the like.

We claim:

1. A polymer formed by a free radical, bulk polymerization of a first hydrophilic monomer conforming to the formula:

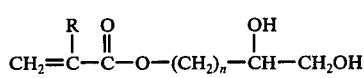

where R is hydrogen or methyl or methyl and $n$ is a whole integer having a value of from 0 to 4,
a second substantially water insoluble monomer conforming to the formula:

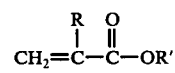

where R is as above described and R' is alkyl having from 1 to 6 carbon atoms,
the mole ratio of said first monomer to said second monomer varying between 1:3 and 20:1, and
a third substantially water insoluble monomer conforming to the formula

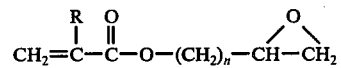

where R and $n$ are as above defined,
the concentration of said third monomer varying between 0 and 30% by weight of the first monomer,
said polymer being insoluble in a member selected from the group of acetone, dioxane and mixtures thereof.

2. The polymer of claim 1 where the mole ratio of the first monomer to the second monomer varies between 1:1 and 10:1.

3. The polymer of claim 2 where the mole ratio varies between 1.2:1 and 2:1.

4. The polymer of claim 1 where the first monomer is 2,3-dihydroxypropyl methacrylate and the second monomer is methyl methacrylate.

5. The polymer of claim 1 where the concentration of the third monomer is at least 0.1 percent by weight of the first monomer.

6. The polymer of claim 5 where the mole ratio of the first monomer to the second monomer varies between 1:1 and 10:1.

7. The polymer of claim 6 where the ratio varies between 1.2:1 and 2:1.

8. The polymer of claim 5 where the concentration of the third monomer varies between 0.1 and 30%.

9. The polymer of claim 8 where the concentration varies between 1 and 15%.

10. The polymer of claim 8 where the concentration varies between 3 and 7%.

11. The polymer of claim 5 where the first monomer is 2,3-dihydroxypropyl methacrylate, the second monomer is methyl methacrylate, the ratio of said first monomer to said second monomer varying between 1:1 and 10:1, and the concentration of said third monomer is sufficient to yield a hydrogel with water having a percent hydration of from 35 to 50% by weight.

12. The polymer of claim 11 where the third monomer is glycidyl methacrylate.

13. The polymer of claim 12 having been formed from said monomeric mixture also including a difunctional acrylate or methacrylate as a crosslinking agent in an amount not exceeding 5% by weight of the total of the monomers.

14. The polymer of claim 13 where the concentration of said crosslinking agent is sufficient to yield a hydrogel with water having a percent hydration of from 42 to 46%.

15. A shaped article from the polymer of claim 1.

16. The shaped article of claim 15 hydrated with water.

17. A shaped article from the polymer of claim 5.

18. The shaped article of claim 17 hydrated with water.

19. The shaped article of claim 18 in the form of a contact lens.

20. A shaped article from the polymer of claim 7.

21. The shaped article of claim 20 hydrated with water.

22. The shaped article of claim 21 in the form of a contact lens.

23. A shaped article from the polymer of claim 11.

24. The shaped article of claim 23 hydrated with water.

25. The shaped article of claim 30 in the form of a contact lens.

26. A shaped article from the polymer of claim 13.

27. The shaped article of claim 26 hydrated with water.

28. The shaped article of claim 27 in the form of a contact lens.

29. The polymer of claim 13 where the difunctional acrylate or methacrylate is ethylene glycol dimethacrylate.

* * * * *